United States Patent
Thacker et al.

(10) Patent No.: US 7,571,001 B2
(45) Date of Patent: Aug. 4, 2009

(54) SYSTEM AND METHOD OF RAPID, COMFORTABLE PARAMETER SWITCHING IN SPINAL CORD STIMULATION

(75) Inventors: James R. Thacker, Eureka, MO (US); John D.H. King, Los Angeles, CA (US); Kerry Bradley, Glendale, CA (US)

(73) Assignee: Boston Scientific Neuromodulation Corporation, Valenica, CA (US)

( * ) Notice: Subject to any disclaimer, the term of this patent is extended or adjusted under 35 U.S.C. 154(b) by 184 days.

(21) Appl. No.: 11/829,742

(22) Filed: Jul. 27, 2007

(65) Prior Publication Data
US 2008/0021513 A1    Jan. 24, 2008

Related U.S. Application Data

(63) Continuation of application No. 10/212,585, filed on Aug. 5, 2002, now Pat. No. 7,263,402.

(60) Provisional application No. 60/311,856, filed on Aug. 13, 2001.

(51) Int. Cl.
*A61N 1/18* (2006.01)
(52) U.S. Cl. .......................... 607/46; 607/117
(58) Field of Classification Search .................... 607/43, 607/46, 117
See application file for complete search history.

(56) References Cited

U.S. PATENT DOCUMENTS

| | | |
|---|---|---|
| 3,646,940 A | 3/1972 | Timm et al. |
| 3,724,467 A | 4/1973 | Avery et al. |
| 3,822,708 A | 7/1974 | Zilber |
| 4,520,825 A | 6/1985 | Thompson et al. |
| 5,370,672 A | 12/1994 | Fowler et al. |
| 5,443,486 A | 8/1995 | Hrdlicka et al. |
| 5,501,703 A | 3/1996 | Holsheimer et al. |
| 5,653,739 A | 8/1997 | Maurer et al. |
| 5,702,429 A | 12/1997 | King |
| 5,938,690 A | 8/1999 | Law et al. |
| 6,052,624 A | 4/2000 | Mann |
| 6,308,102 B1 | 10/2001 | Sieracki et al. |
| 6,381,496 B1 | 4/2002 | Meadows et al. |
| 6,393,325 B1 | 5/2002 | Mann et al. |
| 6,587,724 B2 | 7/2003 | Mann |
| 6,659,968 B1 | 12/2003 | McClure |

*Primary Examiner*—Carl H Layno
*Assistant Examiner*—Brian T Gedeon
(74) *Attorney, Agent, or Firm*—Vista IP Law Group LLP

(57) ABSTRACT

A system and method for rapidly switching stimulation parameters of a Spinal Cord Stimulation (SCS) system increases the number of stimulation parameter sets that may be tested during a fitting procedure, or alternatively, reduces the time required for the fitting procedure. The switching method comprises selecting a new stimulation parameter set, and setting the initial stimulation levels to levels at or just below an estimated perception threshold of the patient. The estimated perception level is based on previous stimulation results. The stimulation level is then increased to determine a minimum stimulation level for effective stimulation, and/or an optimal stimulation level, and/or a maximum stimulation level, based on patient perception.

20 Claims, 7 Drawing Sheets

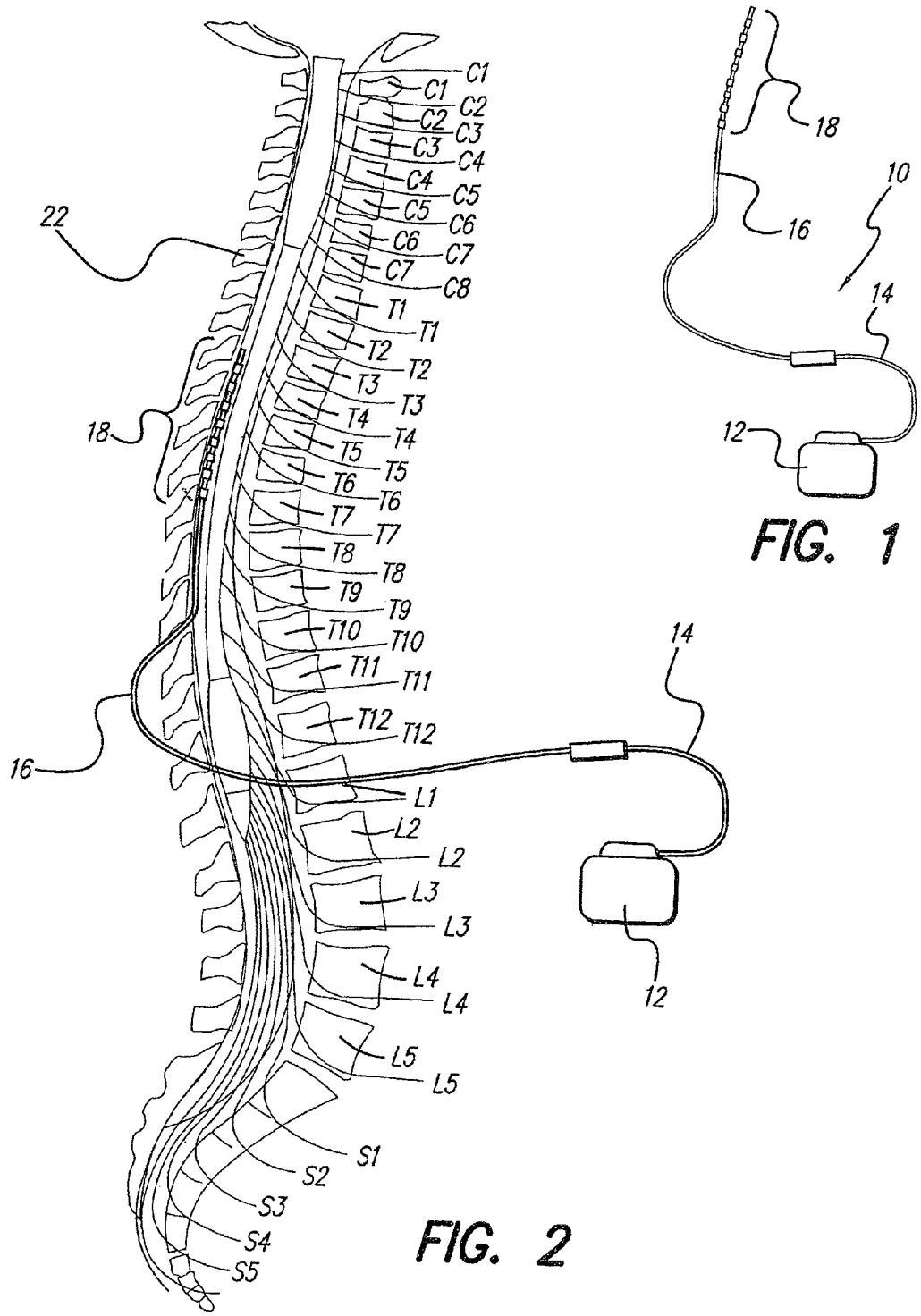

SYSTEM AND METHOD OF RAPID, COMFORTABLE PARAMETER SWITCHING IN SPINAL CORD STIMULATION

RELATED APPLICATIONS

This application is a continuation of U.S. application Ser. No. 10/212,585, now U.S. Pat. No. 7,263,402, filed Aug. 5, 2002, which claims benefit of priority from U.S. Application Ser. No. 60/311,856, filed Aug. 13, 2001. The disclosures of these applications are expressly incorporated herein by reference.

BACKGROUND OF THE INVENTION

The present invention relates to Spinal Cord Stimulation (SCS) systems and more particularly to a system and method for rapidly switching between SCS system stimulation parameter sets. An SCS system treats chronic pain by providing electrical stimulation pulses through the electrodes of an electrode array, which electrode array is placed epidurally next to a patient's spinal cord. The stimulation parameter set specifies both the characteristics of the stimulation pulses provided through the electrode array, and the electrodes used to provide the stimulation pulses. An effective stimulation parameter set for a specific patient may be determined from the response of the patient to various stimulation parameters sets. However, there may be a very large number of stimulation parameter sets, and evaluating all possible sets is very time consuming, and may be impractical.

Spinal cord stimulation is a well accepted clinical method for reducing pain in certain populations of patients. An SCS system typically includes an Implantable Pulse Generator (IPG), electrodes, electrode lead, electrode lead extension, and at least one stimulation parameter set. The electrodes are implanted along the dura of the spinal cord, and the IPG generates electrical pulses which are delivered, through the electrodes, to the fibers of the spinal cord, according to the stimulation parameter set in use. Individual electrode contacts (the "electrodes") are arranged in a desired pattern and spacing in order to create an electrode array. Individual wires within one or more electrode leads connect with each electrode in the array. The electrode leads exit the spinal column and may attach to one or more electrode lead extensions. The electrode lead extensions, or the leads, are typically tunneled around the torso of the patient to a subcutaneous pocket where the IPG is implanted.

Spinal cord stimulators and other stimulation systems are known in the art. For example, an implantable electronic stimulator is disclosed in U.S. Pat. No. 3,646,940 issued Mar. 7, 1972 for "Implantable Electronic Stimulator Electrode and Method" that provides timed sequenced electrical pulses to a plurality of electrodes. As another example, U.S. Pat. No. 3,724,467 issued Apr. 3, 1973 for "Electrode Implant For The Neuro-Stimulation of The Spinal Cord," teaches an electrode implant for the neuro-stimulation of the spinal cord. A relatively thin and flexible strip of physiologically inert plastic is provided as a carrier on which a plurality of electrodes are formed. The electrodes are connected by leads to an RF receiver, which is also implanted.

In U.S. Pat. No. 3,822,708, issued Jul. 9, 1974 for "Electrical Spinal Cord Stimulating Device and Method for Management of Pain," another type of electrical spinal cord stimulation device is taught. The device disclosed in the '708 patent has five aligned electrodes which are positioned longitudinally on the spinal cord. Electrical pulses applied to the electrodes block perceived intractable pain, while allowing passage of other sensations. A patient operated switch allows the patient to adjust the stimulation parameters.

Most of the electrode arrays used with known SCS systems employ between 4 and 16 electrodes. At least two electrodes are selectively programmed to act as anodes and cathodes, creating a bipolar stimulating group, or at least one electrode is selected to cooperate with the IPG case acting as a ground, creating a monopolar stimulation group. The number of stimulation groups available, combined with the ability of integrated circuits to generate a variety of complex stimulation pulses and pulse trains, presents a multiplicity of candidate stimulation parameter sets to the clinician. When an SCS system is implanted, a fitting procedure is performed to select at least one stimulation parameter set for use by the particular patient. The stimulation parameter set is selected for both treatment efficacy, and to minimize power consumption. It is desirable to try as many different stimulation parameter sets as possible during a fitting session in order to increase the likelihood of finding a near optimal set.

A known fitting method is to manually test one parameter set, and then to manually deactivate the stimulation, select a new stimulation parameter set, and then to slowly increase the stimulation level from a zero energy setting until the patient can perceive and assess the effect of the new stimulation parameter set. The testing of each stimulation parameter set is initiated at a zero energy setting. While this is a relatively safe procedure and avoids startling the patient during fitting, it is a slow procedure which prevents large numbers of combinations of parameters from being tested in a reasonable period of time. An alternative approach is to simply switch to a new stimulation parameter set at a stimulation energy setting similar to a level previously exercised. However, even if the new stimulation parameter set provides good results, switching parameter sets abruptly may provide an unpleasant sensation to the patient.

What is therefore needed is a system or method to quickly switch between stimulation parameter sets without causing uncomfortable sensations to the patient.

SUMMARY OF THE INVENTION

The present invention addresses the above and other needs by providing a system or method for rapidly switching between stimulation parameter sets of a Spinal Cord Stimulation (SCS) system, which system or method increases the number of stimulation parameter sets which may be tested during a fitting procedure, or alternatively, reduces the time required for the fitting procedure. The switching system or method comprises the following steps, or means for achieving the following steps: selecting a new stimulation parameter set, setting the initial stimulation level at or below an estimated perception threshold of the patient for the new stimulation parameter set (the perception levels may be estimated based on previous stimulation results), increasing the stimulation level to determine a perceived optimal stimulation level, and/or a perceived maximum stimulation level (i.e., a discomfort level.)

In accordance with one aspect of the invention, there is provided a system or method for rapidly measuring the effectiveness of a large number of stimulation parameter sets. Each new stimulation parameter set is initiated at a stimulation level at, or just below, the estimated perception threshold for the stimulation parameter set, and then increased. As a result, the time required to increase (i.e, ramp up) from a zero energy setting, to the perception threshold, is eliminated.

It is a further feature of the invention to prevent discomfort resulting from initiating a new stimulation parameter set at a perceivable stimulation level. As a result of activating the new stimulation set at or below the perception threshold, the patient has no perception of stimulation upon activation.

It is an additional feature of the invention to facilitate the selection of a low energy level stimulation parameter set. The energy consumption of an SCS system is an important system parameter because high energy consumption may accelerate battery failure and create a requirement for battery replacement. By allowing the comparison of more stimulation parameter sets, a lower energy level stimulation parameter set is more likely to be tested and selected for inclusion in the SCS system.

BRIEF DESCRIPTION OF THE DRAWINGS

The above and, other aspects, features and advantages of the present invention will be more apparent from the following more particular description thereof, presented in conjunction with the following drawings wherein:

FIG. 1 shows a typical Spinal Cord Stimulation (SCS) system;

FIG. 2 depicts the SCS system of FIG. 1 implanted in a spinal column;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Spinal Cord Stimulation (SCS) systems treat chronic pain by providing electrical stimulation pulses through the electrodes of an electrode array, which electrode array is placed epidurally next to a patient's spinal cord. Elements comprising a typical SCS system 10 are shown in FIG. 1. An SCS system 10 typically comprises an Implantable Pulse Generator (IPG) 12, a lead extension 14, an electrode lead 16, and an electrode array 18 residing on a distal end of the lead 16. The IPG 12 generates stimulation pulses for implanted electrodes that make up the electrode array 18. A proximal end of the lead extension 14 is removably connected to the IPG 12 and a distal end of the lead extension 14 is removably connected to a proximal end of the electrode lead 16. The in-series combination of the lead extension 14 and electrode lead 16, carry the stimulation pulses from the IPG 12 to the electrode array 18.

The SCS system 10 described in FIG. 1 above is depicted implanted in a spinal column 22 in FIG. 2. The electrode array 18 is implanted at the site of nerves that are the target of stimulation, e.g., along the spinal cord. Due to the lack of space near the location where the electrode lead 16 exits the spinal column 22, the IPG 12 is generally implanted in the abdomen or above the buttocks. The lead extension 14 facilitates locating the IPG 12 away from the electrode lead exit point.

FIGS. 1 and 2 depict a typical SCS system, and other stimulation systems may utilize different components, utilize similar components organized differently, or be implanted differently. The present invention may be exercised with any stimulation system utilized to treat perceived pain, which system utilizes a lifting procedure to adjust the stimulation parameters to a patient. Therefore, the application of the present invention to any stimulation system is intended to come within the scope of the present invention.

Figure 3A:
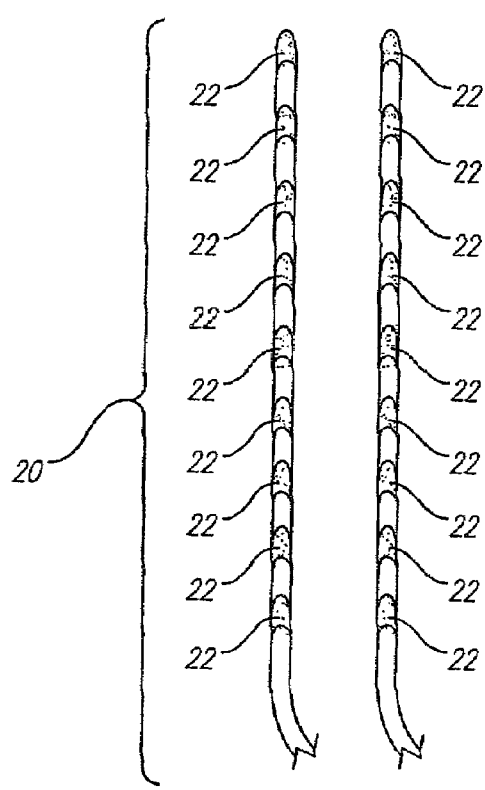
FIG. 3A shows a pair of in-line electrodes used to provide two dimensional stimulation.
Figure 3B:
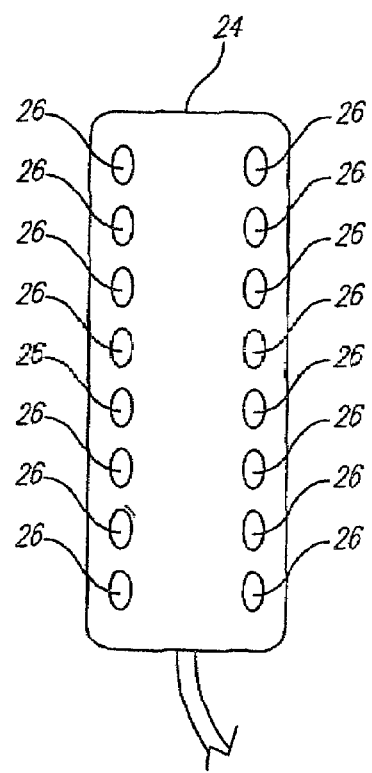
FIG. 3B shows a paddle-type electrode array used to provide two dimensional stimulation.

An SCS system 10 may use a single in-line electrode array (one dimensional) or may use two or more in-line arrays 20 to create a two dimensional array of electrodes 22 as shown in FIG. 3A. An SCS system 10 may also use one or more paddle arrays 24 with two or more columns of electrodes 26 to create a two dimensional array as shown in FIG. 3B. Multiple in-line arrays 20 or a paddle array 24 may be connected to an IPG 12 as shown in FIG. 1.

Figure 4A:
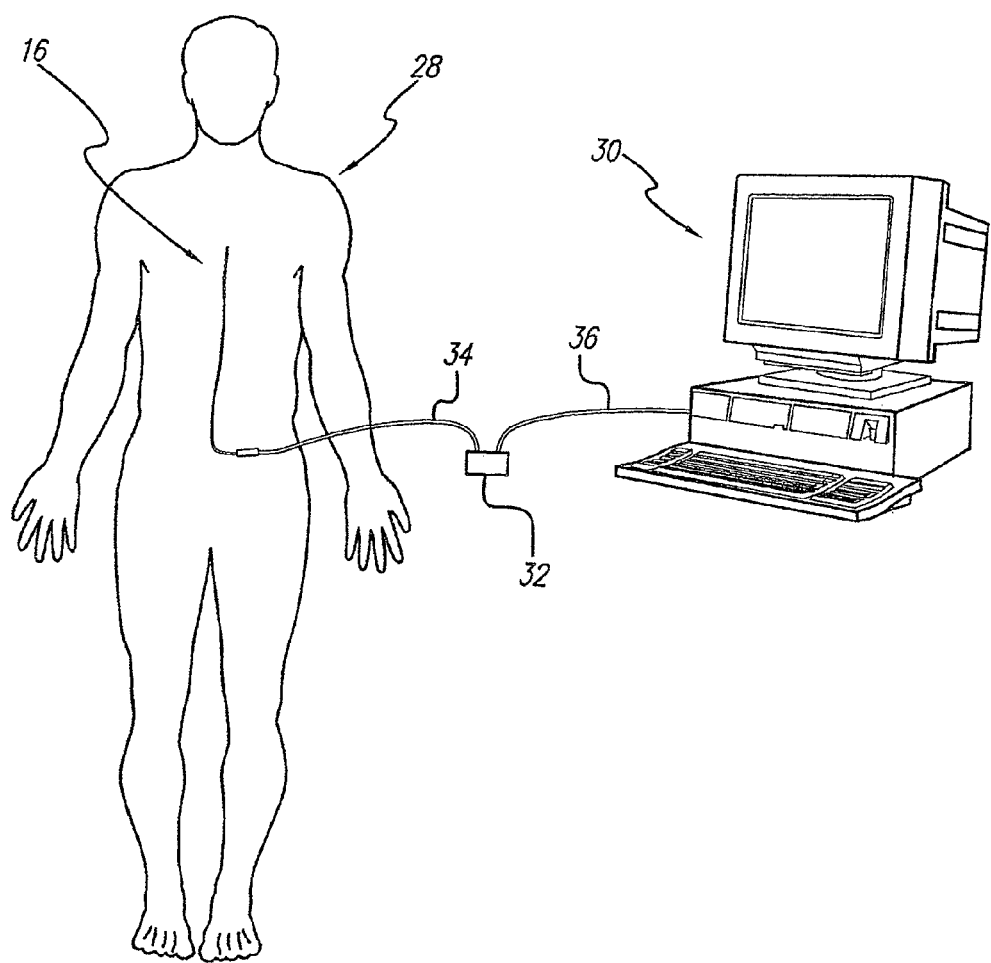
FIG. 4A shows an-equipment suite suitable for an SCS trial phase.

The SCS system 10 is entirely implanted in a patient 28 in normal use, but may be connected to a programming computer 30 during fitting. A fitting suite used during initial implantation is shown in FIG. 4A. During the initial implantation an External Trial Stimulator (ETS) 32 is electrically connected by a transcutaneous cable 34 to the electrode lead 16. A second cable 36 connects the ETS 32 to the programming computer 30.

Figure 4B:
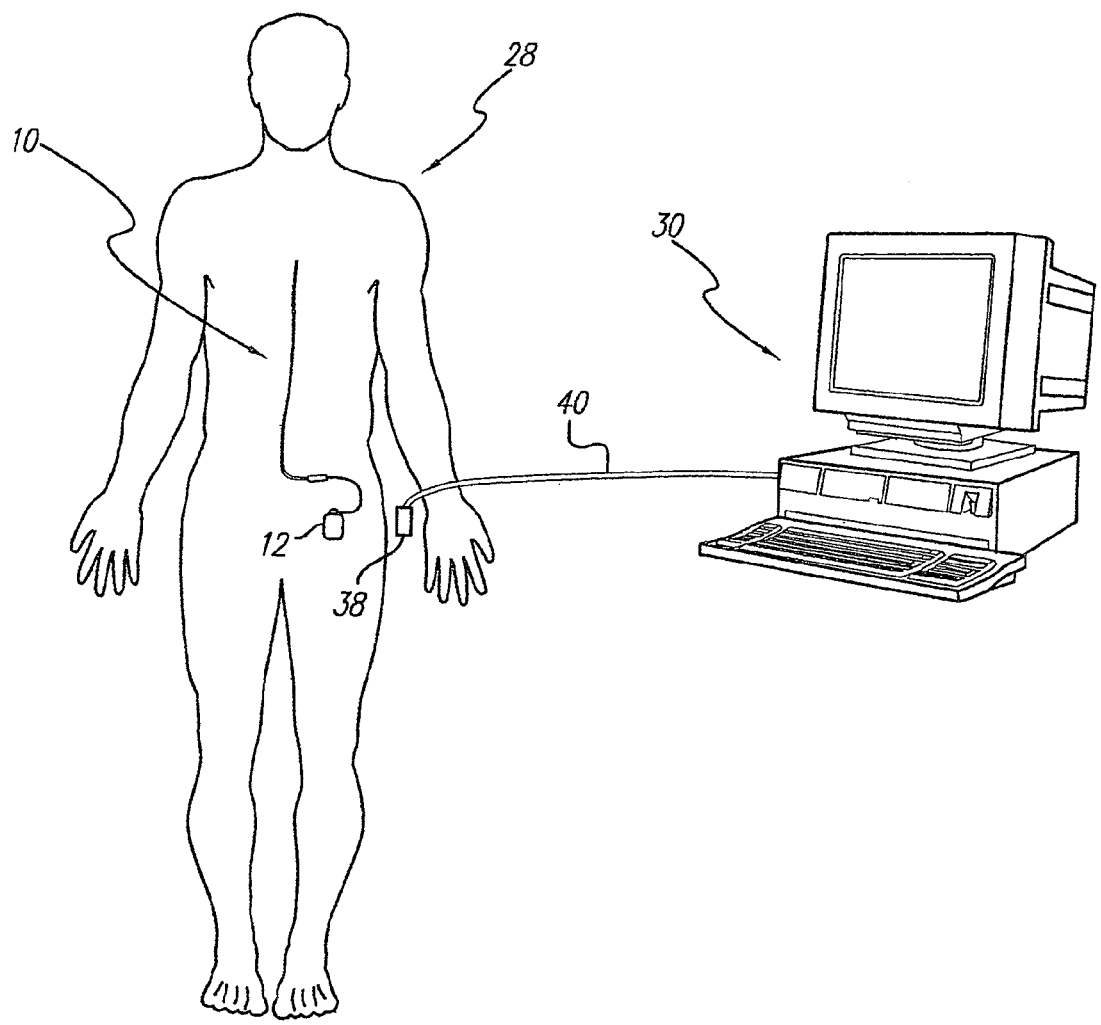
FIG. 4B shows an equipment suite suitable for an SCS fitting phase.

A second fitting suite shown in FIG. 4B is used following implantation of the IPG 12. The second suite includes a hand held programmer (or patient programmer) 38 which wirelessly communicates through the skin with the IPG 12. The programmer 38 also communicates with the programming computer 30 using a third cable 40, an RF link, an IR link, or some other communications technique.

The method of the present invention may be exercised in the context of the first fitting suite, the second fitting suite, or any other system adaptable to the fitting procedure. The exercise of the present invention with any fitting procedure using any equipment is intended to come within the scope of the present invention.

Figure 5:
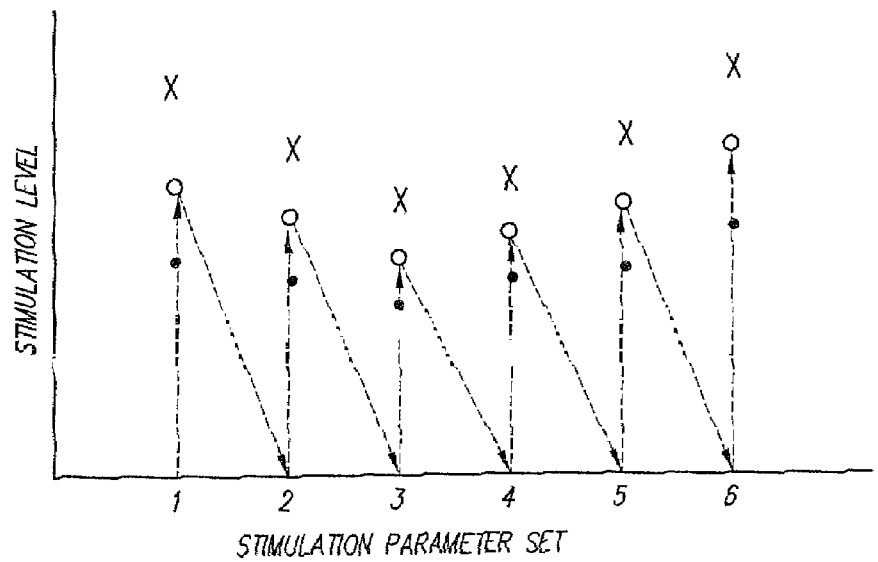
FIG. 5 shows a prior art method of stimulation parameter set switching.

A plot of stimulation level (i.e., energy setting) trajectories for a first known (i.e., prior art) method of measuring the effectiveness of a multiplicity of stimulation parameter sets is depicted in FIG. 5. Each stimulation parameter set comprises a unique combination of electrodes, electrode polarity, relative amplitude, pulse width, and pulse rate. The perception threshold (the stimulation level where the patient starts to feel the effect of the stimulation) is plotted as a solid dot, the optimal stimulation level is plotted as a circle, and the discomfort threshold (the stimulation level where the stimulation itself results in discomfort apart from the pain being treated) is plotted as an "X". The vertical axis is the stimulation level, and the horizontal axis corresponds to different candidate stimulation parameter sets. The stimulation levels are initiated at zero and increased slowly to the perception threshold (i.e., where the patient first feels the stimulation), and on to the optimum stimulation level (i.e., where the patient feels that optimal stimulation has been reached.) Additionally (not shown in FIG. 5), the stimulation level may be further increased to determine the discomfort threshold. As is evident from FIG. 5, the first known method wastes a significant amount of time reaching the perception threshold.

Figure 6:
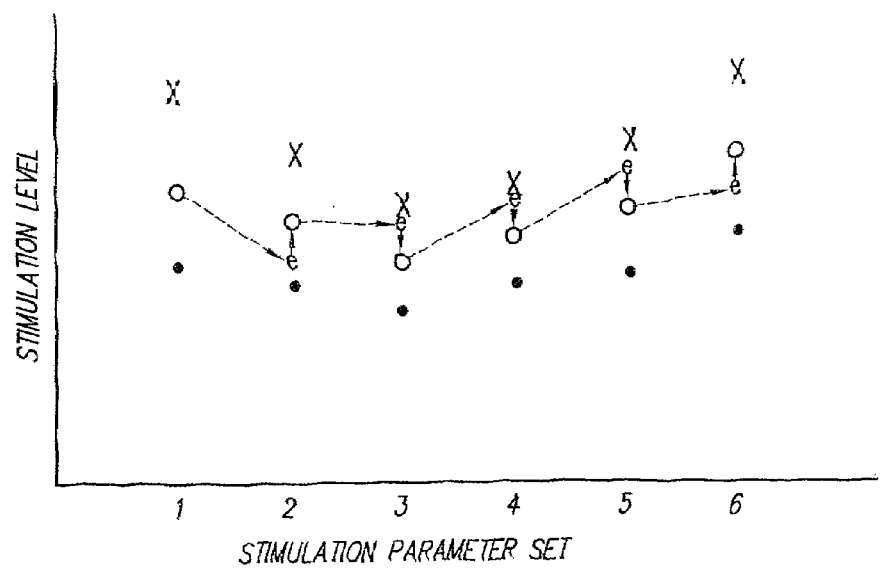
FIG. 6 shows a prior art method of stimulation Rarameter set switching that reduces time, but may produce undesirable side effects.

A plot of a second known (i.e., prior art) method is depicted in FIG. 6. The method of FIG. 6 activates stimulation at an estimate (plotted as an "e") of the optimal stimulation level. The patient or clinician may vary the stimulation level about the estimated optimal level, and locate an optimal level as perceived by the patient. This method eliminates the time spent between the zero stimulation level and the perception threshold, but has a drawback in that initiating the stimulation at a perceivable level of stimulation may cause an unpleasant sensation. Such unpleasant sensation may prejudice the patient against the present stimulation parameter set and against future parameter set switching, and thereby bias the overall results.

Figure 7:
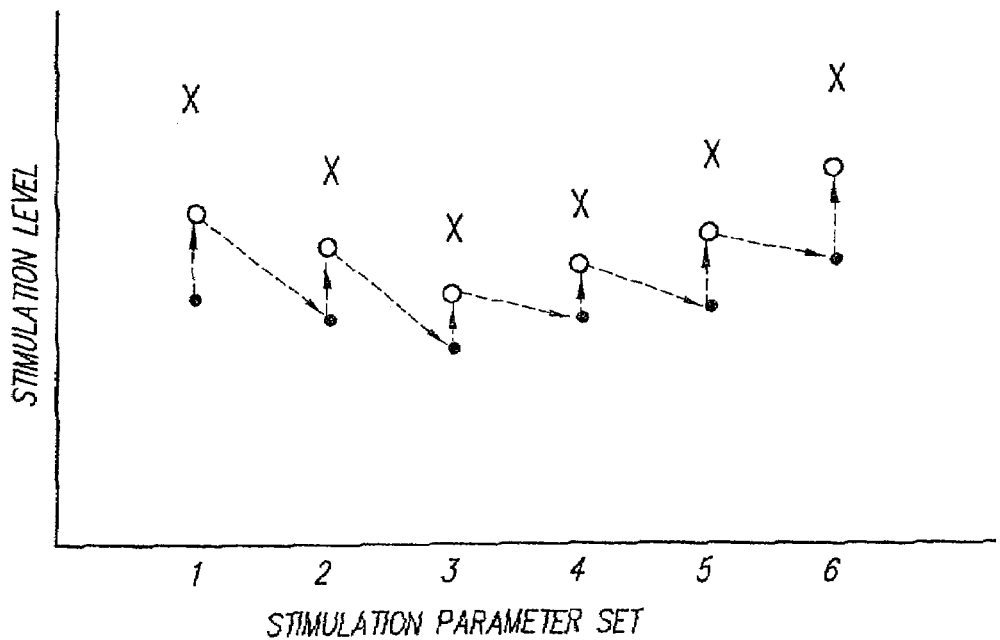
FIG. 7 shows a first embodiment of the present invention wherein the stimulation level is initiated below the perception level and then increased to a perceived optimal level.

A plot of stimulation levels resulting from exercise of a first method of the present invention is depicted in FIG. 7. The first method reduces the time required by known methods to converge to an optimal stimulation level by activating stimulation at a stimulation level at or just below an estimated perception threshold for the stimulation parameter set being tested (i.e., for a trial stimulation parameter set). The trial stimulation parameter set is selected from a set of candidate stimulation parameter sets comprising all of the stimulation parameter sets being considered for the patient. The trial stimulation parameter set is generally an untested candidate stimulation parameter set. After initiating stimulation, the stimulation level is then increased as shown in FIG. 7, and the patient indicates, for example, when a perceived optimal stimulation level is reached, thereby providing a measurement of the optimal stimulation level for the trial stimulation parameter set. The stimulation level may also be varied around the optimal stimulation level to ensure that the level first identified by the patient is truly the optimal level. The patient may also indicate when the perception threshold is reached, and/or when the discomfort threshold is reached.

After the optimal stimulation levels have been measured for all of the candidate stimulation parameter sets, the stimulation may be switched between two or more candidate stimulation parameter sets to determine which set provides the best results. In these cases, stimulation may be activated at or just below the stimulation threshold, and then the stimulation level may be increased manually or automatically to the optimal stimulation level measured previously for the candidate stimulation parameter set being exercised.

Because energy consumption is an important parameter of an implantable stimulation system, the energy consumptions of the candidate stimulation parameter sets may be recorded at the minimum effective stimulation level and/or optimal stimulation level of each candidate stimulation parameter set. Following the testing of all of the candidate stimulation parameter sets, a candidate stimulation parameter set providing effective stimulation with a low energy consumption may be selected as the stimulation parameter set to be used by the patient. Alternatively, one of a plurality of candidate stimulation parameter sets providing similar optimal stimulation results may be selected based on the energy consumption required for optimal stimulation.

A method for obtaining estimates of the perception thresholds by measuring a subset of perception thresholds, and then estimating (e.g., by interpolating) the perception thresholds for each untested stimulation parameter set, is described in U.S. Pat. No. 6,393,325 issued May 21, 2002 for "Directional Programming for Implantable Electrode Arrays." The '325 patent is incorporated herein by reference.

Figure 8:
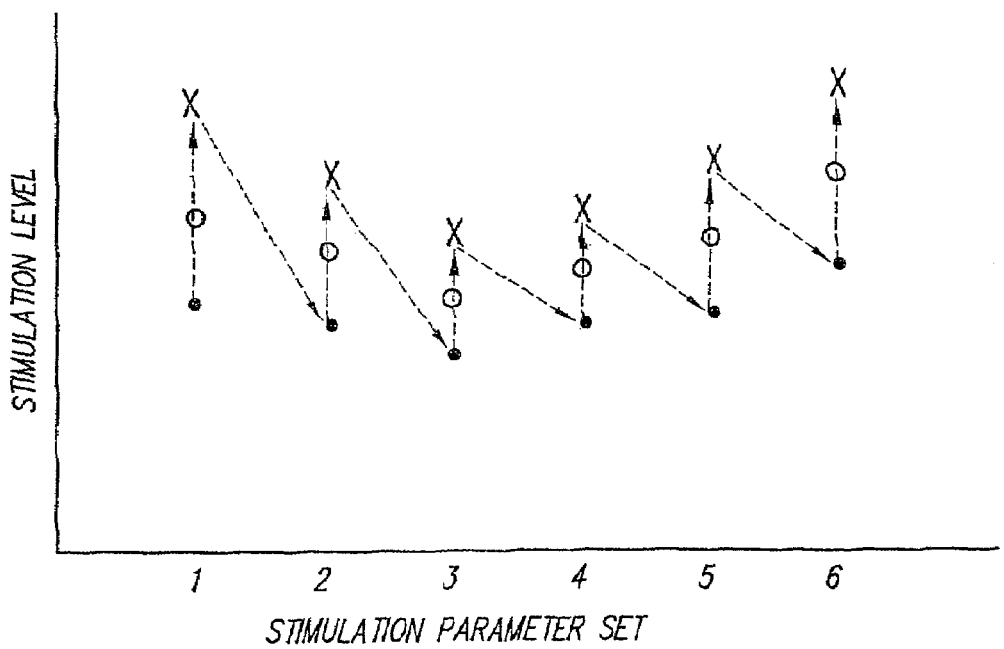
FIG. 8 shows a second embodiment of the present invention wherein the stimulation level is initiated below the perception level and increased to a perceived maximum level.

A plot of stimulation levels resulting from exercise of a second embodiment of the present invention, wherein the discomfort threshold is being investigated, the stimulation level trajectories are as shown in FIG. 8. Stimulation is activated at or just below the perception threshold, as in FIG. 7, but instead of only searching for the optimal stimulation level, the stimulation level is increased until the patient indicates that the stimulation is resulting in discomfort independent of the pain being treated.

In the embodiments described in FIGS. 7 and 8, the methods may be modified by varying the stimulation level around the optimal stimulation level, and/or the discomfort threshold, to fine tune the measurement of the optimal stimulation level, and/or the discomfort threshold. The patient may directly vary the stimulation level, or a clinician may vary the stimulation level based on observations by the patient. Further, as the perception thresholds for additional stimulation parameter sets are measured, the methods of the '325 patent may be reapplied to refine the estimated perception thresholds for stimulation parameter sets yet to be tested.

Figure 9:
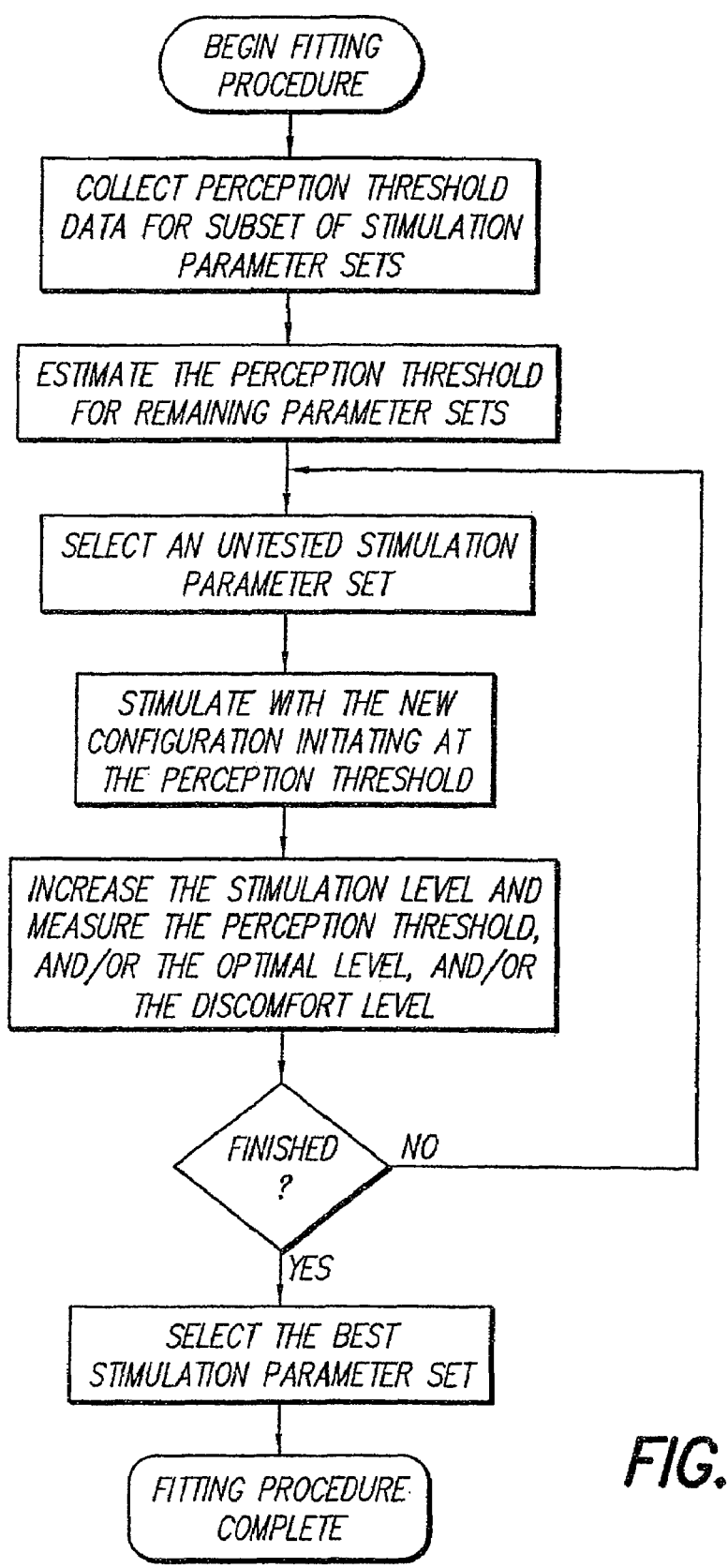
FIG. 9 shows a flow chart of an embodiment of the method taught herein.

A method for carrying out the present invention is depicted in FIG. 9 and may be described as including the following steps:

Testing a subset of candidate stimulation parameter sets;
Collecting perception level data for the tested candidate stimulation parameter sets;
Using the perception level data collected to estimate the perception level for the untested candidate stimulation parameter sets;
Selecting a trial stimulation parameter set from the untested stimulation parameter set;
Providing stimulation using the trial stimulation parameter set using the estimated perception threshold as the initial stimulation level;
Increasing the stimulation level;
Measuring the perception threshold, and/or the optimal stimulation level, and/or the discomfort threshold, and/or the energy consumption at the optimal stimulation level for the trial stimulation parameter set;
Selecting an untested candidate stimulation parameter set as a new trial stimulation parameter set, and repeating the above; and
After all of the candidate stimulation parameter sets have been tested, selecting the best candidate stimulation parameter set.

The method described in FIG. 9 may further include the following: Varying the stimulation level to refine the perception threshold, and/or the optimal stimulation level, and/or the discomfort level;
Recording the perception threshold, and /or the optimal stimulation level, and/or the discomfort level, and/or the energy consumption at the optimal stimulation level; or
Holding the stimulation level at a fixed stimulation level to characterize the effect of stimulation at the fixed stimulation level for a short period of time.

The basis for selecting the best candidate stimulation parameter set may be one of the measured parameters, or a combination of the measured stimulation parameters. Also, more than one candidate stimulation parameter set may be selected, wherein the patient may control which one of a set of stimulation parameter sets is executed at any given time.

Those skilled in the art will recognize that other applications of stimulation will benefit from the present invention, (e.g., stimulation to relieve migraine headaches, or peripheral nerve stimulation) and the use of the present invention with those other applications is intended to come within the scope of the present invention. Further, the present invention applies to measuring the effectiveness of any of the stimulation parameters, where activation above the perception threshold may cause unpleasant sensations, and is not intended to be limited to the variation of any specific parameter.

As described above, the present invention allows rapid manual or automatic switching between stimulation parameter sets, while avoiding unpleasant side effects that may result from activating stimulation at a perceivable stimulation level. The method applies to measurement of the minimum stimulation level required for effective stimulation, the optimal stimulation level, and the discomfort threshold for a stimulation parameter set. Further, the method may be applied to comparing the effectiveness of several stimulation parameter sets. A stimulation system, and in particular an SCS system 10, may thus include at least one stimulation parameter set selected from a multiplicity of candidate stimulation sets, wherein the stimulation system provides stimulation based on efficiently comparing the performance of all of the multiplicity of stimulation parameter sets.

While the invention herein disclosed has been described by means of specific embodiments and applications thereof, numerous modifications and variations could be made thereto by those skilled in the art without departing from the scope of the invention set forth in the claims.

What is claimed is:

1. A stimulation system fitting suite, comprising:
   a pulse generator configured for generating stimulation pulses according to stimulation commands;
   a lead connected to the pulse generator, wherein the lead is configured for carrying the stimulation pulses;
   an electrode array carried by the lead, wherein the electrode array is configured for receiving the stimulation pulses from the lead;
   a programming computer configured for:
      selecting a new stimulation parameter set with a new combination of electrodes or electrode polarity;
      selecting an initial stimulation level for the new stimulation parameter set, wherein the initial stimulation level is selected to be a non-zero value not to exceed an estimated perception threshold of a patient for the new stimulation parameter set;
      generating initial stimulation commands based on the new stimulation parameter set and the selected initial stimulation level;
      generating new stimulation commands based on the new stimulation parameter set and an increased stimulation level; and
      providing the initial stimulation commands and the new stimulation commands to the pulse generator.

2. The stimulation system fitting suite of claim 1, wherein the programming computer is configured for estimating the perception threshold of the patient.

3. The stimulation system fitting suite of claim 2, wherein the programming computer is configured for estimating the perception threshold of the patient based on a previously recorded effect of stimulation pulses on the patient.

4. The stimulation system fitting suite of claim 1, wherein the non-zero value is a value at or just below the estimated perception threshold of the patient for the new stimulation parameter set.

5. The stimulation system fitting suite of claim 1, wherein the new combination of electrodes or electrode polarity comprises a new subset of electrodes.

6. The stimulation system fitting suite of claim 1, wherein the programming computer is configured for recording the effect of the stimulation pulses on the patient.

7. The stimulation system fitting suite of claim 6, wherein the programming computer is configured for recording the effect of the stimulation pulses on the patient by recording a perception threshold for the new stimulation parameter set.

8. The stimulation system fitting suite of claim 6, wherein the programming computer is configured for recording the effect of the stimulation pulses on the patient by recording an optimal stimulation level for the new stimulation parameter set.

9. The stimulation system fitting suite of claim 6, wherein the programming computer is configured for recording the effect of the stimulation pulses on the patient by recording a discomfort threshold for the new stimulation parameter set.

10. The stimulation system fitting suite of claim 6, wherein the programming computer is configured for recording the effect of the stimulation pulses on the patient by measuring an energy consumption required for effective stimulation for the new stimulation parameter set.

11. The stimulation system fitting suite of claim 6, wherein the programming computer is configured for recording the effect of the stimulation pulses on the patient by:
    measuring at least one of a set consisting of a perception threshold, an optimal stimulation level, a discomfort threshold, and an energy consumption required for effective stimulation; and
    varying the stimulation level around an initial measurement to improve the measurement.

12. The stimulation system fitting suite of claim 1, wherein the programming computer is configured for holding the stimulation level at a fixed stimulation level to characterize the effect of stimulation pulses on the patient at the fixed stimulation level for a short period of time.

13. The stimulation system fitting suite of claim 1, wherein the programming computer is further configured for:
    selecting a second new stimulation parameter set;
    selecting an initial stimulation lead level for the second new stimulation parameter set, wherein the initial stimulation level is selected so as to be a non-zero value not to exceed an estimated perception threshold of the patient for the second new stimulation parameter set;
    generating initial stimulation commands based on the second new stimulation parameter set and the selected initial stimulation level;
    generating second new stimulation commands based on the second new stimulation parameter set and an increased stimulation level; and
    providing the second new stimulation commands to the pulse generator.

14. The stimulation system fitting suite of claim 1, wherein the programming computer is further configured for:
    collecting perception level data for a subset of a multiplicity of stimulation parameter sets; and
    using the collected perception level data to estimate the perception level for untested stimulation parameter sets.

15. A stimulation system fitting suite, comprising:
    a pulse generator configured for generating stimulation pulses according to stimulation commands;
    a lead connected to the pulse generator, wherein the lead is configured for carrying the stimulation pulses;
    an electrode array carried by the lead, wherein the electrode array is configured for receiving the stimulation pulses from the lead;
    a programming computer, for each of a group of candidate stimulation parameter sets, configured for:

selecting a trial stimulation parameter set with a new combination of electrodes or electrode polarity from a group of candidate stimulation parameter sets;

selecting an initial stimulation level for the trial stimulation parameter set, wherein the initial stimulation level is selected to be a non-zero value not to exceed an estimated perception threshold of a patient for the trial stimulation parameter set;

generating initial stimulation commands based on the new stimulation parameter set and the selected initial stimulation level;

generating new stimulation commands based on the new stimulation parameter set and an increased stimulation level;

providing the initial stimulation commands and the new stimulation commands to the pulse generator; and measuring the effectiveness-of the stimulation pulses on the patient; and selecting the preferred stimulation parameter set based on measured effectiveness.

16. The stimulation system fitting suite of claim 15, wherein the programming computer is configured for estimating the perception threshold of the patient.

17. The stimulation system fitting suite of claim 15, wherein the programming computer is configured for measuring the effectiveness of the stimulation parameter set comprises recording observations made by the patient on the effect of the stimulation pulses.

18. The stimulation system fitting suite of claim 15, wherein the programming computer is configured for measuring the effectiveness of the stimulation parameter set by measuring at least one of a set consisting of a perception level, an optimal stimulation level, a discomfort threshold, and an energy consumption required for effective stimulation, wherein the measuring is based on observations made by the patient on the effect of the stimulation pulses.

19. The stimulation system fitting suite of claim 15, wherein the programming computer is configured for selecting the stimulation parameter set with the preferred effectiveness by retesting at least two previously tested stimulation parameter sets to compare the effectiveness of each of the at least two previously tested stimulation parameter sets to the effectiveness of others of the at least two previously tested stimulation parameter sets, wherein each stimulation parameter set is initiated at a stimulation level selected to be a non-zero value not to exceed the perception threshold of the patient, and then the stimulation level is increased to a level the comparison is to be made at.

20. The stimulation system fitting suite of claim 15, wherein the programming computer is configured for, after measuring the effectiveness of the stimulation parameter set, using the measurement of the perception threshold obtained for the tested stimulation parameter set to improve the estimated perception threshold for untested stimulation parameter sets.

* * * * *